United States Patent
Sugiura

(10) Patent No.: US 10,669,669 B2
(45) Date of Patent: Jun. 2, 2020

(54) DEODORANT AND DEODORIZING PRODUCT

(71) Applicant: TOAGOSEI CO., LTD., Minato-ku (JP)

(72) Inventor: Koji Sugiura, Nagoya (JP)

(73) Assignee: TOAGOSEI CO., LTD., Minato-ku (JP)

( * ) Notice: Subject to any disclaimer, the term of this patent is extended or adjusted under 35 U.S.C. 154(b) by 321 days.

(21) Appl. No.: 15/515,925

(22) PCT Filed: Sep. 14, 2015

(86) PCT No.: PCT/JP2015/076060
§ 371 (c)(1),
(2) Date: Mar. 30, 2017

(87) PCT Pub. No.: WO2016/103807
PCT Pub. Date: Jun. 30, 2016

(65) Prior Publication Data
US 2017/0306554 A1    Oct. 26, 2017

(30) Foreign Application Priority Data

Dec. 24, 2014  (JP) .................. 2014-261314

(51) Int. Cl.
| | |
|---|---|
| *A61L 9/01* | (2006.01) |
| *D06M 13/00* | (2006.01) |
| *B01J 20/06* | (2006.01) |
| *B01J 20/08* | (2006.01) |
| *D06M 11/44* | (2006.01) |
| *D06M 11/45* | (2006.01) |

(52) U.S. Cl.
CPC .......... *D06M 13/005* (2013.01); *A61L 9/01* (2013.01); *B01J 20/06* (2013.01); *B01J 20/08* (2013.01); *D06M 11/44* (2013.01); *D06M 11/45* (2013.01)

(58) Field of Classification Search
CPC ...................................... A61L 9/01
See application file for complete search history.

(56) References Cited

U.S. PATENT DOCUMENTS

| 5,110,586 A | 5/1992 | Kurihara et al. |
| 2015/0023903 A1 | 6/2015 | Ando et al. |

FOREIGN PATENT DOCUMENTS

| CN | 1231929 A | 10/1999 |
| CN | 1380054 A | 11/2002 |

(Continued)

OTHER PUBLICATIONS

Combined Chinese Office Action and Search Report dated Dec. 26, 2018 in Chinese Patent Application No. 2015800522609.6 (with English translation and English translation of Category of Cited Documents), 13 pages.

(Continued)

*Primary Examiner* — Andrew T Piziali
(74) *Attorney, Agent, or Firm* — Oblon, McClelland, Maier & Neustadt, L.L.P.

(57) ABSTRACT

The deodorant of the present invention is characterized in that the deodorant consists of a crystalline zinc oxide in which zinc oxide and aluminum oxide are composited, and a molar ratio ($ZnO/Al_2O_3$) of the zinc oxide to the aluminum oxide is in a range from 40 to 80. The deodorant has a high deodorizing effect against sulfur gases and acidic gases. A preferable average particle size of the deodorant is 0.2 to 15 µm.

16 Claims, 1 Drawing Sheet

(56) References Cited

FOREIGN PATENT DOCUMENTS

| | | | |
|---|---|---|---|
| CN | 103476707 A | 12/2013 |
| CN | 104254348 A | 12/2014 |
| EP | 0 358 821 A1 | 3/1990 |
| JP | 63-246167 A | 10/1988 |
| JP | 1-171555 A | 7/1989 |
| JP | 5-237375 A | 9/1993 |
| JP | 11-35381 A | 2/1999 |
| JP | 2002-95727 A | 4/2002 |
| JP | 2002-126057 A | 5/2002 |
| JP | 2003-24424 A | 1/2003 |
| JP | 2003-52800 A | 2/2003 |
| JP | 2005-21825 A | 1/2005 |
| JP | 2005-87630 A | 4/2005 |
| JP | 2006-199659 A | 8/2006 |
| JP | 2006-223645 A | 8/2006 |
| JP | 2008-125810 A | 6/2008 |

OTHER PUBLICATIONS

International Search Report dated Dec. 22, 2015 in PCT/JP2015/076060 Filed Sep. 14, 2015.
Office Action dated Feb. 18, 2019 in corresponding Taiwanese Patent Application No. 104133688 (with English Translation), 6 pages.

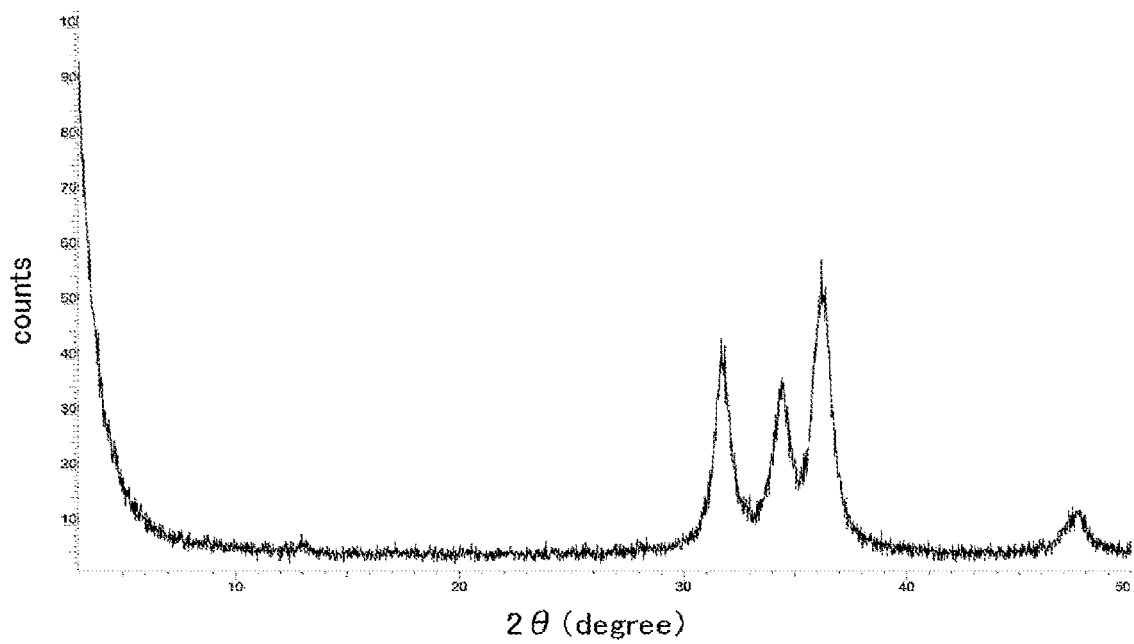

DEODORANT AND DEODORIZING PRODUCT

TECHNICAL FIELD

The present invention relates to a deodorant that consists of a specific crystalline zinc oxide, and has high deodorizing capacity, and to a deodorizing product including the same.

BACKGROUND ART

In recent years, public interest in odor in daily life has grown, and stationary-type deodorizing products, spray-type deodorizing products, and various other deodorizing products (e.g., wallpaper, curtain, carpet, mat, sofa, filter, and clothes) that are provided with a deodorizing effect have been put on the market in order to deal with a demand for a reduction in an unpleasant odor or an offensive odor. A specific deodorant is used for these deodorizing products depending on the type of unpleasant odor.

For example, Patent Document 1 discloses a deodorant for a sulfur-based gas that includes an amorphous composite of a salt of at least one metal selected from copper, zinc, manganese, cobalt, and nickel, and a silicate, and has a pore volume of 0.3 to 0.5 ml/g. Patent Document 2 discloses a deodorant that has a structure in which a copper compound represented by $nCuO.MY_2/x.mH_2O$ (wherein n is ⅓ to 9, M is a divalent metal atom, Y is a monovalent anion, divalent anion, or a trivalent anion, x is a valence of the anion, and m is a number from 0 to 18) is supported on an inorganic solid acid having an acid strength function Ho of +4.8 or less and an acidity of 0.2 meq/g or more, and that is suitable for deodorizing an acidic gas or a basic gas, and.

Patent Document 3 discloses a deodorant that consists of a zinc EDTA, and that is suitable for deodorizing an ammonia-based gas or a sulfur-based gas. Patent Document 4 discloses a deodorant that includes a zinc salt of a branched fatty acid having 9 to 32 carbon atoms, and that is suitable for deodorizing a sulfur-based gas or an acidic gas.

Patent Document 5 discloses a honeycomb-like formed body obtained by forming an aluminum-containing zinc phyllosilicate or a silicic acid composite thereof and describes that the honeycomb-like formed body is suitable for deodorizing an ammonia-based gas or a sulfur-based gas.

Patent Document 6 discloses a deodorant that consists of a composite metal polybasic salt represented by $Zn_aM^2{}_bM^3{}_x(OH)_y(A)_z.nH_2O$, and that is suitable for deodorizing an amine-based gas, an acidic gas, or a sulfur-based gas.

A deodorant that includes zinc oxide as the main component is also known. For example, Patent Document 7 discloses a deodorant that consists of a fine zinc oxide having a specific surface area of 40 to 100 $m^2/g$, a hydrogen sulfide deodorizing capacity of 3.0 mmol/g, and a primary particle size of 0.2 μm or less, and that is suitable for deodorizing a sulfur-based gas. Patent Document 8 discloses a deodorant that consists of particles in which zinc oxide and either or both of aluminum oxide and silicon oxide are closely bonded, and that is suitable for deodorizing an ammonia-based gas, an amine-based gas, or a sulfur-based gas. Patent Document 9 discloses a deodorant that includes a zinc oxide-based solid solution represented by $Zn_{1-x}Al_xO$ (0<x<0.2) and a composite metal silicate, and that is suitable for deodorizing an ammonia-based gas or a sulfur-based gas.

PRIOR TECHNICAL DOCUMENT

Patent Document

[Patent Document 1] JP-A 2005-87630
[Patent Document 2] JP-A H5-237375
[Patent Document 3] JP-A 2002-95727
[Patent Document 4] JP-A 2008-125810
[Patent Document 5] JP-A H11-35381
[Patent Document 6] JP-A 2002-126057
[Patent Document 7] JP-A 2003-52800
[Patent Document 8] JP-A S63-246167
[Patent Document 9] JP-A 2006-223645

SUMMARY OF THE INVENTION

Problems that the Invention is to Solve

Deodorants that include various inorganic compounds are known as described above. When a deodorizing product includes a deodorant consisting of a copper compound having a blue color, for example, a part that exhibits a deodorant effect normally has a color close to blue so that the intended performance is obtained. Specifically, when the deodorant is colored, the color of the deodorant may not fit the image of the deodorizing product, and it may be difficult to provide a deodorizing product that exhibits the desired deodorizing effect.

A deodorant consisting of a zinc oxide is known as a deodorant with white color or an approximately white color (e.g., light yellow), and a deodorant having a higher deodorizing effect than that of publicly known zinc oxide has been desired.

Means for Solving the Problems

The inventor found that a higher deodorizing effect can be obtained by improving zinc oxide that has a deodorizing effect on a sulfur-based gas and an acidic gas. The inventor also found that a cloth, a thread, and the like that include a deodorant consisting of the improved zinc oxide exhibit a high deodorizing effect without showing a problem with respect to the outward appearance (e.g., change in color).

Specifically, one aspect of the present invention is a deodorant that consists of a crystalline zinc oxide in which zinc oxide and aluminum oxide are composited, wherein the molar ratio ($ZnO/Al_2O_3$) of the zinc oxide to the aluminum oxide is 40 to 80.

Another aspect of the present invention is a deodorizing product having the above deodorant.

Effects of the Invention

The deodorant of the present invention exhibits a high deodorizing effect through chemical adsorption, and is excellent in deodorizing effect on a sulfur-based gas and an acidic gas. The deodorant of the present invention is in white-based color, and can be used in a convenient manner. Since the deodorant of the present invention exhibits excellent processability, a deodorizing product for various applications, a deodorant-containing coating composition that forms a deodorant coating or the like, a deodorant-containing resin composition that forms a resin molded article or a foamed article, and the like can be provided by utilizing the deodorant of the present invention.

BRIEF DESCRIPTION OF DRAWINGS

FIG. 1 illustrates an X-ray diffraction chart of the deodorant used in Example 1.

EMBODIMENTS FOR CARRYING OUT THE INVENTION

Hereinafter, the present invention is described in detail.

The deodorant of the present invention consists of a crystalline zinc oxide in which zinc oxide and aluminum oxide are composited.

A molar ratio ($ZnO/Al_2O_3$) of the zinc oxide to aluminum oxide is in a range from 40 to 80, preferably from 35 to 70, and more preferably from 35 to 50, from a viewpoint of a deodorizing effect on a sulfur-based gas and an acidic gas.

It is considered that the crystalline zinc oxide has specific crystallinity due to the inclusion of a specific amount of aluminum oxide, and the specific crystallinity contributes to an excellent deodorizing performance with respect to a sulfur-based gas and an acidic gas since a sulfur-based gas and an acidic gas are easily adsorbed in the present invention.

The crystalline zinc oxide that is a deodorant of the present invention shows crystallinity when subjected to X-ray powder diffraction analysis. When the crystalline zinc oxide of the present invention is subjected to X-ray powder diffraction analysis, diffraction peaks attributed to the crystal structure of zinc oxide are observed in the resulting X-ray diffraction chart at about 31.7 degrees, about 34.4 degrees, and about 36.2 degrees (i.e., within a range in which the diffraction angle $2\theta$ is 30 to 38 degrees). A diffraction intensity of each peak differs depending on the measurement conditions. However, a half width of each diffraction peak is almost identical irrespective of the diffraction intensity. The half width of each peak is normally in a range from 0.5 to 1.1 degrees, and preferably from 0.7 to 0.9 degrees. Since a particle size of the crystalline zinc oxide is normally 100 nm or larger, the half width in the X-ray diffraction chart indicates crystallinity instead of the crystal grain size. The crystalline zinc oxide according to the present invention is characterized in that it is not a crystal that has excellent crystallinity, but has a specific crystallinity that differs from an amorphous state.

A shape of the deodorant of the present invention is not particularly limited, but is preferably particulate since a high deodorizing effect is obtained when the deodorant is used for a deodorant coating (including a deodorant point), a resin molded article, a foamed article, and the like, and a deodorant-containing coating composition or a deodorant-containing resin composition for producing these deodorant coating and the like exhibits excellent processability. In this case, an average particle size of the deodorant is preferably in a range from 0.2 to 15 μm, more preferably from 0.3 to 12 μm, and further preferably from 0.5 to 8 μm. The maximum particle size of the deodorant is normally 20 μm or smaller, and preferably 15 μm or smaller. The average particle size refers to a particle size d50 measured by laser diffractometry.

A BET specific surface area of the deodorant of the present invention is preferably 100 $m^2/g$ or more, more preferably in a range from 110 to 200 $m^2/g$, and further preferably from 120 to 160 $m^2/g$. The deodorant having the specific surface area of 100 $m^2/g$ or more exhibits a high deodorizing effect.

The crystalline zinc oxide according to the invention is in white-based color. According to the Lab color space, the deodorant (powder) has preferably an L value of 92 to 98, an a value of −1 to −6, and a b value of 4 to 10, and more preferably an L value of 94 to 97, an a value of −1.5 to 5, and a b value of 5 to 9.

A deodorizing capacity of the deodorant consisting of the crystalline zinc oxide in the present invention is preferably 50 ml/g or more with respect to hydrogen sulfide gas, 3 ml/g or more with respect to methyl mercaptan gas, and 20 ml/g or more with respect to acetic acid gas. The term "deodorizing capacity" used herein refers to the maximum amount of an odor component (i.e., hydrogen sulfide, methyl mercaptan, or acetic acid) that can be deodorized, absorbed, or adsorbed by the deodorant. The deodorizing capacity is measured as described below. The deodorant is put in a test bag (e.g., Tedlar (registered trademark) bag) that is formed of a material on which the odor component is rarely adsorbed and which does not allow air to pass through. After sealing the test bag, an odor gas is injected into the test bag. The odor gas concentration in the test bag is measured immediately after the odor gas has been injected, and after a given time has elapsed. A time at which the residual gas concentration measured after a given time has elapsed has become equal to or less than 1/10th of the initial gas concentration is determined to be a breakpoint with respect to the deodorizing performance, and the difference between the residual gas concentration and the initial gas concentration is taken as the amount of odor gas that has been deodorized, absorbed, or adsorbed by the deodorant. A deodorant having a deodorizing capacity of less than the above-described preferred value has low deodorizing performance and an insufficient deodorizing effect.

A production method of the deodorant consisting of the crystalline zinc oxide according to the present invention is not particularly limited. An arbitrary raw material, production process, equipment, and the like may be used to produce the deodorant. An outline of a method for producing the crystalline zinc oxide is described below.

An aqueous slurry containing a zinc oxide particle in an amount of 1% to 20% by mass is prepared, and then colloidal alumina in a ratio of 1% to 4% by mass based on the zinc oxide particle is added to the slurry while stirring. Subsequently a temperature of the mixture is adjusted to 20° C. to 60° C., and carbon dioxide gas is introduced into the mixture for several hours to prepare a basic zinc carbonate particle including aluminum oxide inside of the particle. After that, water is removed from the resulting slurry containing the basic zinc carbonate particle to obtain a dry powder, which is heated at a temperature from about 100° C. to about 400° C. to obtain crystalline zinc oxide aggregates having the above configuration. The crystalline zinc oxide aggregates are pulverized to obtain a crystalline zinc oxide powder that is suitably used as the deodorant of the present invention.

The deodorant of the present invention has a deodorizing effect, and may be put in a container (e.g., cartridge) in the form of a powder or granules to produce a deodorizing product, for example. When the deodorizing product is placed in the vicinity of an indoor or outdoor offensive odor emission source, the concentration of a component that emits an unpleasant odor or an offensive odor can be reduced. The deodorant of the present invention may be used in combination with other materials to produce a deodorizing product used for various applications, a deodorant-containing coating composition that forms a deodorant coating or the like, a deodorant-containing resin composition that forms a resin molded article or a foamed article, and the like (as described in detail below).

One example of a useful deodorizing product that utilizes the deodorant of the present invention is a deodorizing fiber. Examples of the deodorizing fiber include a deodorizing fiber (1) in which the deodorant adheres to, or is bonded to, the surface of a raw material fiber, and a deodorizing fiber (2) in which the deodorant is embedded in a raw material fiber so as to be exposed from the surface of the raw material fiber. The raw material fiber may be a natural fiber or a synthetic fiber. The raw material fiber may be a short fiber, a long fiber, a composite fiber having a sheath-core structure, or the like. The deodorizing fiber (1) may be obtained by applying a deodorant-containing liquid composition such as an aqueous or organic solvent-based suspension that includes the deodorant to the surface of a raw material fiber using a coating method, a dipping method, or the like, and removing the medium (e.g., solvent). The deodorant-containing liquid composition may contain an adhesive that improves the adhesion of the deodorant to the surface of the raw material fiber. The pH of the aqueous suspension including the deodorant is not particularly limited, but is preferably adjusted to about 6 to 8 so that the deodorant exhibits sufficient performance.

The deodorizing fiber (2) may be obtained by adding the deodorant of the present invention to a molten liquid of a resin for forming fibers, or a resin solution of a resin for forming fibers in which the resin is dissolved, and forming a fiber using the resulting deodorant-containing resin composition. The resin for forming fibers used for this method is not particularly limited, but a resin constituting publicly known chemical fiber may be used. Examples of a preferable resin include a polyester resin, a polyamide resin, an acrylic resin, a polyethylene resin, a polyvinyl resin, a polyvinylidene resin, a polyurethane resin, a polystyrene resin, and the like. These resins may be a homopolymer or a copolymer. When the resin is a copolymer, the monomers may be polymerized in an arbitrary ratio.

A content of the deodorant in the deodorant-containing resin composition is not particularly limited. It is normally possible to obtain a higher deodorizing performance, and maintain the deodorizing performance for a long time by increasing the content of the deodorant. However, a significant difference in deodorizing effect may not occur even when the content of the deodorant is increased to a large extent, or the strength of the deodorizing fiber may be decreased when the content of the deodorant is increased to a large extent. Therefore, the content is preferably in a range from 0.1 to 20 parts by mass, and more preferably from 0.5 to 10 parts by mass based on 100 parts by mass of the resin for forming fibers.

The deodorizing fiber having the deodorant of the present invention may be used for a textile product such as clothes (e.g., underwear, sock, and apron), nursing clothes, bedclothes, a cushion, a blanket, a carpet, a sofa, an air filter, a quilt cover, a curtain, a car seat, and a product obtained by processing the deodorant sheet described later.

Another major application for the deodorant of the present invention is the deodorant-containing coating composition as mentioned above. An oil/fat or a resin used as the main component of a vehicle that is used in case of producing the deodorant-containing coating composition is not particularly limited. A natural vegetable oil, a natural resin, a semi-synthetic resin, or a synthetic resin may be used. Examples of the oil/fat and the resin include a drying oil and a semi-drying oil such as linseed oil, Chinese tung oil, and soybean oil, rosin, cellulose nitrate, ethyl cellulose, cellulose acetate butyrate, benzyl cellulose, a novolac-type or resol-type phenolic resin, an alkyd resin, an amino-alkyd resin, an acrylic resin, a vinyl chloride resin, a silicone resin, a fluororesin, an epoxy resin, a urethane resin, a saturated polyester resin, a melamine resin, a polyvinylidene chloride resin, and the like. The deodorant-containing coating composition may be a thermoplastic composition or a thermosetting composition.

A content of the deodorant of the present invention in the deodorant-containing coating composition is not particularly limited. It is normally possible to obtain a higher deodorizing performance, and maintain the deodorizing performance for a long time by increasing the content of the deodorant. However, a significant difference in deodorizing effect may not occur even when the content of the deodorant is increased to a large extent, or the coating surface may lose its gloss, or cracks may be formed when the content of the deodorant is increased to a large extent. Therefore, the content of the deodorant is preferably in a range from 0.1% to 20% by mass, and more preferably from 0.5% to 10% by mass based on a total amount of the composition.

The deodorant of the present invention can be used for both a liquid coating material and a powdery coating material. The deodorant-containing coating composition may be designed to form a coating through an arbitrary mechanism. When it is desired to cure the resulting coating, the deodorant-containing coating composition may be an oxidatively polymerizable composition, a moisture polymerizable composition, a thermally curable composition, a catalytically curable composition, a UV-curable composition, a polyol-curable composition, or the like. An additive (e.g., pigment and dispersant) that may be added to the composition is not particularly limited as long as the additive does not undergo a chemical reaction with the deodorant of the present invention. The deodorant-containing coating composition can be easily prepared. Specifically, the deodorant-containing coating composition can be prepared by sufficiently dispersing and mixing the raw material components using an ordinary mixing device such as ball mill, roll mill, disperser, and mixer.

The deodorant-containing coating composition containing the deodorant of the present invention may suitably be used for (applied to) an inner wall or outer wall of a building, a vehicle, a railroad vehicle, and the like; a garbage incineration plant; a garbage container; and the like.

A further application of the deodorant of the present invention is a deodorizing sheet (including a deodorizing film). A raw material sheet for the deodorizing sheet is not particularly limited. A material for forming the raw material sheet, the microscopic structure of the raw material sheet, and the like may be selected taking account of the application and the like. The raw material sheet is preferably formed of an organic material such as a resin and paper, an inorganic material, or a composite material of these. It is preferable that the raw material sheet allow air to pass through from one side to the other side. A raw material sheet formed of is also preferably used. Specific examples of a preferable raw material sheet include Japanese paper, a synthetic paper, a nonwoven fabric, a resin film, and the like. It is particularly preferable that the raw material sheet be a paper formed of either or both of a natural pulp and a synthetic pulp. When a natural pulp is used, the deodorant particle easily enters the space between the fibers that are finely branched, and a practical carrier (support) can be obtained without using a binder. On the other hand, a synthetic pulp exhibits excellent chemical resistance. When the synthetic pulp is used, it may be difficult to support the deodorant particle (powder) between the fibers. In order to suppress the occurrence of such a situation, part of the fibers may be melted in a drying step that is performed after papermaking so that the adhesion between the powder and the fibers increases, or fibers formed of another thermosetting resin may be mixed. Paper for which various properties are adjusted can be obtained by utilizing natural pulp and synthetic pulp in an appropriate ratio. It is normally possible to obtain paper that exhibits excellent strength, water resistance, chemical resistance, oil resistance, and the like by increasing the ratio of synthetic pulp, and obtain paper that exhibits excellent water absorption, gas permeability, hydrophilicity, formability, texture, and the like by increasing the ratio of natural pulp.

The deodorizing sheet may have a structure in which the deodorant is included in the entire raw material sheet from one side to the other side, or may have a structure in which the deodorant is provided in a surface layer situated on one side or the other side of the raw material sheet, or may have a structure in which the deodorant is provided only inside the raw material sheet.

A supporting amount of the deodorant of the present invention included in the deodorizing sheet is not particularly limited. It is normally possible to obtain a higher deodorizing performance, and maintain the deodorizing performance for a long time by increasing the content of the deodorant. However, a significant difference in deodorizing effect may not occur even when the amount of deodorant supported on the deodorizing sheet is increased to a large extent. Therefore, the supporting amount of the deodorant is preferably in a range from 0.1 to 10 parts by mass based on 100 parts by mass of the raw material sheet.

A production method of the deodorizing sheet is not particularly limited. The deodorant of the present invention may be supported when producing the raw material sheet, or may be supported after producing the raw material sheet. For example, the deodorant may be supported in paper by applying a method that introduces the deodorant in an arbitrary step of the papermaking process, a method that applies the deodorant-containing liquid composition including an adhesive to paper that has been produced in advance using a coating method, an immersion method, or a spray method, or the like. It is preferable to apply the deodorant-containing liquid composition so that the deodorant is supported in an amount of about 0.05 to 10 g/m$^2$.

Hereinafter, a method that introduces the deodorant during a papermaking process is described as an example of a method for producing a deodorizing sheet in which the deodorant of the present invention is supported on paper. The papermaking process may be performed according to a publicly known method. First, a slurry including the deodorant and pulp in a specific ratio is prepared, and then a cationic flocculant and an anionic flocculant are added to the slurry respectively in a ratio of 5% or less by mass based on a total amount of the slurry to produce an aggregate (flock). Subsequently, the aggregate is subjected to the papermaking process according to a publicly known method. After that, the resulting paper is dried at a temperature from 100° C. to 190° C. to obtain a deodorizing sheet in which the deodorant is supported on paper.

The deodorizing sheet having the deodorant of the present invention may be used as a medical packing paper, a food packing paper, an electric device packing paper, a nursing paper product, a freshness-keeping paper, paper clothes, an air-cleaning filter, a wallpaper, a tissue, a toilet paper, and the like.

The deodorant of the present invention may be applied to a resin molded article or a foamed article, as described above. The resin molded article is produced using the deodorant-containing resin composition as a molding material. The deodorant-containing resin composition may be a mixture or a molten mixture that includes a thermoplastic resin and the deodorant. The resin molded article can be produced by charging the deodorant-containing resin composition into a molding machine. A pellet-like resin containing the deodorant at a high concentration may be prepared in advance, and mixed with the main resin, and the mixture may be charged into a molding machine. An additive such as a pigment, a dye, an antioxidant, a light stabilizer, an antistatic agent, a blowing agent, an impact modifier, glass fibers, a dampproof agent and an extender may optionally be added to the deodorant-containing resin composition in order to improve the properties of the deodorant-containing resin composition. The resin molded article or the foamed article may be produced by applying an ordinary molding method such as injection molding method, extrusion molding method, inflation molding method, vacuum forming method, and expansion molding method.

The resin molded article or the foamed article that includes the deodorant of the present invention may be used as (for) a home appliance (e.g., air cleaner and refrigerator), a common household product (e.g., trash box and drainer), a nursing product (e.g., portable toilet), and the like.

EXAMPLES

Hereinafter, the present invention is specifically described using Examples. The present invention is not limited to the Examples.

1. Production and Evaluation of Deodorant

In the following Examples 1 to 3 and Comparative Examples 1 to 4, deodorants (d1) to (d7) were respectively produced, and each item was analyzed or evaluated using the methods described later. The results are listed in Table 1.

Example 1

Colloidal alumina was added to an aqueous slurry containing zinc oxide (10% by mass) in a mass ratio of 3% by mass based on the zinc oxide, and then carbon dioxide gas was introduced into the slurry (mixture) at a temperature of 40° C. for 6 hours while stirring. Subsequently the slurry was dried at 105° C. to remove water from the slurry. The dried product was heated at 300° C. to obtain a powder of crystalline zinc oxide in which the zinc oxide and aluminum oxide were composited. The resulting crystalline zinc oxide powder was used as the deodorant (d1). The composition, the particle sizes d50 and d90, the specific surface area, the half width, the color values, and the deodorizing capacity of the deodorant (d1) are listed in Table 1.

Example 2

A powder of crystalline zinc oxide was obtained in the same manner as those in Example 1, except that the colloidal alumina was used in a mass ratio of 3.7% by mass based on the zinc oxide. The resulting crystalline zinc oxide powder was used as the deodorant (d2). The analysis results and the evaluation results for the deodorant (d2) are listed in Table 1.

Example 3

A powder of crystalline zinc oxide was obtained in the same manner as those in Example 2, except that the heating temperature was changed to 250° C. The resulting crystalline zinc oxide powder was used as the deodorant (d3). The analysis results and the evaluation results for the deodorant (d3) are listed in Table 1.

Comparative Examples 1 to 3

Commercially-available type II zinc oxide (JIS standard), activated zinc oxide, and ultrafine zinc oxide were respectively used as the deodorants (d4) to (d6). The analysis results and the evaluation results for each deodorant are listed in Table 1.

Comparative Example 4

A solution prepared by dissolving 37.5 g of No. 2 sodium silicate in 100 ml of deionized water, and a solution prepared by dissolving 17.75 g of zinc sulfate pentahydrate in 100 ml of deionized water, were simultaneously added dropwise to 75 ml of deionized water over 1 hour while stirring. After the dropwise addition, the mixture was stirred for 1 hour to obtain a slurry (pH: 6.8) including a white precipitate (reaction product). The slurry was filtered under reduced pressure through a glass filter on which a microfilter having a pore size of 0.5 μm was placed, and the reaction product was washed with deionized water, and subjected to suction filtration to collect the reaction product. Subsequently, the reaction product was dried at a temperature of 150° C. for 24 hours, and pulverized to obtain a zinc silica gel powder. The resulting zinc silica gel powder was used as the deodorant (d7). The analysis results and the evaluation results for the deodorant (d7) are listed in Table 1.

poration to obtain an X-ray diffraction chart. The tube voltage was set to 40 kV, and the current was set to 150 mA as measurement conditions. FIG. 1 illustrates the X-ray diffraction chart of the deodorant (d1). In FIG. 1, three diffraction peaks between 30 and 38 degrees are attributed to zinc oxide. The half width of the peak at about 31.8 degrees was calculated. The peak width at 50% of the peak height was taken as the half width.

(5) Color of Deodorant Powder

The deodorant powder was put in a 10 ml glass bottle, and the color of the deodorant powder was measured using a color difference meter "SZ-Σ80" (type name) manufactured by Nippon Denshoku Industries Co., Ltd. The results were indicated using the Lab color space.

(6) Deodorizing Performance with Respect to Methyl Mercaptan 0.01 g of the dried deodorant powder was put in a test bag produced using a vinyl alcohol-based polymer film. After injecting 1 liter of methyl mercaptan (initial concentration: 600 ppm) into the test bag, the test bag was sealed, and allowed to stand for 30 minutes. The residual gas concentration in the test bag was then measured using a gas detecting tube.

TABLE 1

| | | Deodorant | d50 | d90 | Specific surface area | Half width | Color | Deodorizing capacity |
|---|---|---|---|---|---|---|---|---|
| | | Composition or type | (μm) | (μm) | (m$^2$/g) | (deg) | L/a/b | (ml/g) |
| Example 1 | d1 | Al$_2$O$_3$•65ZnO•2.2H$_2$O* | 1.2 | 6.4 | 130 | 0.8 | 97.2/−3.4/7.3 | 18 |
| Example 2 | d2 | Al$_2$O$_3$•54ZnO•1.9H$_2$O* | 1.5 | 5 | 148 | 0.8 | 96.9/−3.5/7.3 | 16 |
| Example 3 | d3 | Al$_2$O$_3$•54ZnO•3.4H$_2$O* | 1.7 | 6.5 | 108 | 1.0 | 96.9/−2.4/6.1 | 10 |
| Comparative Example 1 | d4 | Type II zinc oxide | 0.3 | 0.7 | 0.4 | 0.2 | 96.4/−0.2/2.0 | 1 |
| Comparative Example 2 | d5 | Activated zinc oxide | 9.9 | 28.6 | 64 | 0.5 | 96.8/−0.2/2.8 | 2 |
| Comparative Example 3 | d6 | Ultrafine zinc oxide | 0.1 | 0.5 | 250 | 0.4 | 95.2/−2.7/5.8 | 2 |
| Comparative Example 4 | d7 | Zinc silica gel | 10.9 | 31.1 | 178 | — | 92.5/0.5/−1.7 | 1 |

*"H$_2$O" refers to sorbed water.

Analysis and evaluation method for the deodorants (d1) to (d7) are as described below.

(1) Elemental Composition

The Al/Zn molar ratio was calculated using an X-ray fluorescence spectrometer "ZSX100e" (type name) manufactured by Rigaku Corporation.

(2) Particle Sizes d50 and d90

The particle sizes d50 and d90 of the deodorant were analyzed (on a volume basis) using a laser diffraction particle size analyzer "MS2000" (type name) manufactured by Malvern. Note that the content in the particle size distribution is the volume ratio based on all of the particles. Since the density of the measurement target powder is constant, the content in the particle size distribution is the same as the value on a mass basis.

(3) Specific Surface Area

The specific surface area was measured using a surface area analyzer "SA-6200" (type name) manufactured by Horiba Ltd. in accordance with JIS Z 8830-2001 ("Determination of the specific surface area of powders (solids) by gas adsorption-BET method").

(4) Half Width of X-Ray Diffraction Peak

X-ray powder diffraction analysis (in which CuKα-rays were used) was performed using an X-ray diffractometer "RINT2400V" (type name) manufactured by Rigaku Cor- As is clear from the results in Table 1, the deodorants (d1) to (d3) of Examples 1 to 3 (deodorants of the present invention) exhibited excellent deodorizing performance with respect to methyl mercaptan.

2. Production and Evaluation of Deodorizing Product (1)

Example 4

2 parts by mass of the deodorant (d1) and 100 parts by mass of an acrylic binder dispersion having a solid content of 2% by mass were mixed to obtain a deodorant-containing liquid composition. The deodorant-containing liquid composition was applied to a cloth formed of polyester fibers so that the deodorant (d1) was spread in an amount of 1 g/m$^2$ to obtain a deodorizing cloth.

The deodorizing cloth was cut to obtain a test cloth having a size of 10×10 cm, and the test cloth was put in a test bag produced using a vinyl alcohol-based polymer film. After injecting 3 liters of acetic acid (initial concentration: 30 ppm) or hydrogen sulfide (initial concentration: 4 ppm) into the test bag, the test bag was allowed to stand for 2 hours. The residual gas concentration in the test bag was then measured using a gas detecting tube, and the reduction ratio was calculated. The results are listed in Table 2.

Example 5

A deodorizing cloth was produced in the same manner as those in Example 4 except using the deodorant (d2) instead of the deodorant (d1), and the deodorizing test was performed in the same manner as in Example 4. The results are listed in Table 2.

Comparative Example 5

A deodorizing cloth was produced in the same manner as those in Example 4 except using the deodorant (d4) instead of the deodorant (d1), and the deodorizing test was performed in the same manner as in Example 4. The results are listed in Table 2.

Comparative Example 6

A deodorizing cloth was produced in the same manner as those in Example 4 except using the deodorant (d5) instead of the deodorant (d1), and the deodorizing test was performed in the same manner as in Example 4. The results are listed in Table 2.

TABLE 2

|  | Acetic acid | Hydrogen sulfide |
| --- | --- | --- |
| Example 4 | >99% | >99% |
| Example 5 | >99% | >99% |
| Comparative Example 5 | 19% | 5% |
| Comparative Example 6 | 69% | 74% |

3. Production and Evaluation of Deodorizing Product (2)

Example 6

10 parts by mass of the deodorant (d1) and 90 parts by mass of a polyester resin for forming fibers were melt-mixed, and the mixture was pelletized to obtain a masterbatch consisting of a thermoplastic resin composition. Subsequently, 20 parts by mass of the masterbatch and 80 parts by mass of a polyester resin for forming fibers were mixed, and the mixture was spun to obtain a 75d/72f multifilament containing the deodorant (d1) in an amount of 2% by mass. 1 g of the multifilament was put in a test bag produced using a vinyl alcohol-based polymer film. After injecting 3 liters of acetic acid (initial concentration: 30 ppm) or methyl mercaptan (initial concentration: 8 ppm) into the test bag, the test bag was allowed to stand for 2 hours. The residual gas concentration in the test bag was then measured using a gas detecting tube, and the reduction ratio was calculated. The reduction ratio of acetic acid was 88%, and the reduction ratio of methyl mercaptan was 78%.

As is clear from the results obtained in Examples 4 to 6, the deodorizing products obtained using the deodorant of the present invention exhibited excellent deodorizing effect on an odorous gas.

INDUSTRIAL APPLICABILITY

The deodorant of the present invention exhibits a high deodorizing effect through chemical adsorption, and exhibits an excellent deodorizing effect on a sulfur-based gas and an acidic gas. The deodorant of the present invention is in white-based color, and can be used in a convenient manner. Since the deodorant of the present invention exhibits excellent processability, a deodorizing product used for various applications, a deodorant-containing coating composition that produces a deodorant coating or the like, a deodorant-containing resin composition that produces a resin molded article or a foamed article, and the like can be produced by utilizing the deodorant. The deodorizing product produced by utilizing the deodorant is useful as a wallpaper, a filter (e.g., mask filter and air-conditioner filter), a carpet, a mat, a sofa, a curtain, a cover, clothes, an ornament, a food freshness-keeping material, and the like that are used to deodorize an animal odor, an excretion odor, a foul odor (including an odor emitted from a pet or pet supplies), and the like that occur (indoors and outdoors) at a medical/nursing/excretion site, a sewage plant, a refuse disposal plant (incineration plant), a fertilizer plant, a chemical plant, a cattle farm, a fishing port, an animal-related facility, a food processing-related facility, and the like.

The invention claimed is:

1. A deodorant, consisting of:
   pulverized aggregates of a crystalline zinc oxide having particles of aluminum oxide therein,
   wherein
   a molar ratio of zinc oxide to aluminum oxide in the in the pulverized aggregates of crystalline zinc oxide is from 40 to 80,
   wherein the crystalline zinc oxide when subjected to an X-ray powder diffraction analysis using CuKα-rays has diffraction peaks comprising a diffraction peak at 31.8 degrees, and
   a half width of the diffraction peak at 31.8 degrees ranges from 0.5 to 1.1 degrees.

2. The deodorant according to claim 1, wherein the crystalline zinc oxide has an average particle size of 0.2 to 15 μm.

3. The deodorant according to claim 1, wherein the crystalline zinc oxide has a BET specific surface area of 100 m$^2$/g or more.

4. A deodorizing product, comprising the deodorant according to claim 1.

5. The deodorant according to claim 1, wherein
   the crystalline zinc oxide when subjected to an X-ray powder diffraction analysis has diffraction peaks within a range in which a diffraction angle 2θ is from 30 to 38 degrees, and
   a half width of each of the diffraction peaks ranges from 0.5 to 1.1 degrees.

6. The deodorizing product according to claim 4, which is a deodorizing fiber, wherein
   the deodorizing fiber further comprises a fiber, and
   the deodorant either is embedded in the fiber or adheres to or is bonded to a surface of the fiber.

7. The deodorizing product according to claim 6, wherein the fiber is formed from a resin, and
   a content of the deodorant is from 0.1 to 20 parts by mass based on 100 parts by mass of the resin forming the fiber.

8. The deodorizing product according to claim 4, which is a deodorant-containing coating composition, wherein a content of the deodorant is from 0.1 to 20% by mass based on a total mass of the composition.

9. The deodorizing product according to claim 4, which is a deodorizing sheet.

10. The deodorizing product according to claim 4, which is a deodorant-containing resin composition comprising a thermoplastic resin, the deodorant, and optionally at least one additive selected from the group consisting of a pigment, a dye, an antioxidant, a light stabilizer, an antistatic agent, a blowing agent, an impact modifier, glass fibers, a dampproof agent, and an extender.

11. The deodorant according to claim 1, wherein the crystalline zinc oxide has a "L" value of 92 to 98, an "a" value of −1 to −6, and a "b" value of 4 to 10 according to Lab color space.

12. A deodorant, consisting of:
pulverized aggregates of a crystalline zinc oxide having particles of aluminum oxide therein,
wherein a molar ratio of zinc oxide to aluminum oxide is in a range of from 40 to 80, and wherein the crystalline zinc oxide when subjected to an X-ray powder diffraction analysis using CuKα-rays has three diffraction peaks within a range in which a diffraction angle 2θ is from 30 to 38 degrees, and
wherein a half width of each of the diffraction peaks ranges from 0.5 to 1.1 degrees.

13. The deodorant according to claim 12, wherein the crystalline zinc oxide has an average particle size of 0.2 to 15 μm.

14. The deodorant according to claim 12, wherein the crystalline zinc oxide has a BET specific surface area of 100 m$^2$/g or more.

15. The deodorant according to claim 12, wherein the crystalline zinc oxide has a "L" value of 92 to 98, an "a" value of −1 to −6, and a "b" value of 4 to 10 according to Lab color space.

16. A deodorizing product, comprising the deodorant according to claim 12.

* * * * *